United States Patent
Iitsuka

(10) Patent No.: US 11,806,024 B2
(45) Date of Patent: Nov. 7, 2023

(54) SURGICAL BUR

(71) Applicant: NAKANISHI INC., Kanuma (JP)

(72) Inventor: Takamitsu Iitsuka, Kanuma (JP)

(73) Assignee: NAKANISHI INC., Kanuma (JP)

( * ) Notice: Subject to any disclaimer, the term of this patent is extended or adjusted under 35 U.S.C. 154(b) by 33 days.

(21) Appl. No.: 17/551,738

(22) Filed: Dec. 15, 2021

(65) Prior Publication Data

US 2022/0409213 A1    Dec. 29, 2022

(30) Foreign Application Priority Data

Jun. 24, 2021   (JP) ................................. 2021-104515

(51) Int. Cl.
*A61B 17/16*   (2006.01)

(52) U.S. Cl.
CPC ................................ *A61B 17/1615* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1655; A61B 17/1657; A61B 17/1659
See application file for complete search history.

(56) References Cited

U.S. PATENT DOCUMENTS

| | | | |
|---|---|---|---|
| 5,759,185 A * | 6/1998 | Grinberg | B23C 5/28 606/180 |
| 8,460,298 B2 * | 6/2013 | O'Donoghue | A61B 17/1615 606/80 |
| 9,179,923 B2 * | 11/2015 | Gubellini | A61B 17/1615 |
| 11,039,852 B2 * | 6/2021 | Nishio | A61B 17/320725 |
| 2009/0048602 A1 * | 2/2009 | O'Donoghue | A61B 17/1615 606/80 |
| 2012/0150209 A1 * | 6/2012 | Gubellini | A61B 17/1615 606/170 |
| 2015/0297243 A1 * | 10/2015 | Kulas | A61B 17/1695 606/80 |
| 2016/0287267 A1 * | 10/2016 | Kulas | A61B 17/1617 |
| 2018/0256174 A1 * | 9/2018 | Deeny | A61B 17/1615 |
| 2019/0209203 A1 * | 7/2019 | Nishio | A61B 17/320758 |
| 2022/0409213 A1 * | 12/2022 | Iitsuka | A61B 17/1615 |

FOREIGN PATENT DOCUMENTS

| | | | |
|---|---|---|---|
| JP | 2013-138820 | 7/2013 | |
| WO | WO-2011023381 A1 * | 3/2011 | ......... A61B 17/1615 |
| WO | WO-2018069579 A2 * | 4/2018 | ............. A61B 17/14 |
| WO | WO-2022123548 A1 * | 6/2022 | |

* cited by examiner

*Primary Examiner* — Eric S Gibson
(74) *Attorney, Agent, or Firm* — Rankin, Hill & Clark LLP

(57) ABSTRACT

A surgical bur includes a shaft portion that rotates in a rotation direction about a rotation axial line of the surgical cutting bur, and a cutting portion that is provided at a distal end of the shaft portion. In the surgical bur, the cutting portion has a spherical shape, has abrasive grains on a surface of the cutting portion, and has a first vertical groove extending from a distal end side of the cutting portion in an axial direction.

9 Claims, 5 Drawing Sheets

FIG. 4A
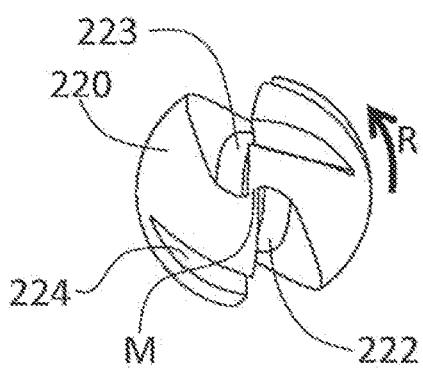
FIG. 4B
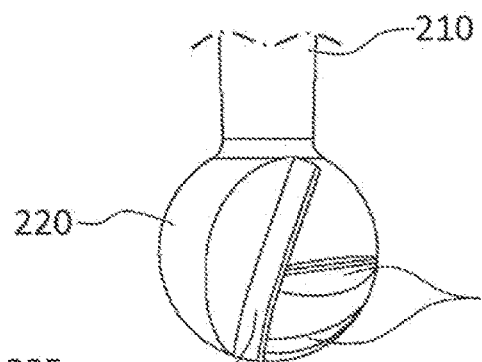
FIG. 4C
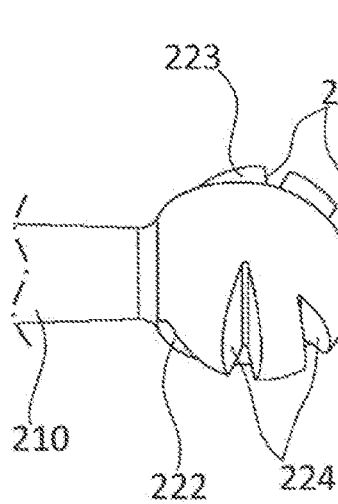
FIG. 4E
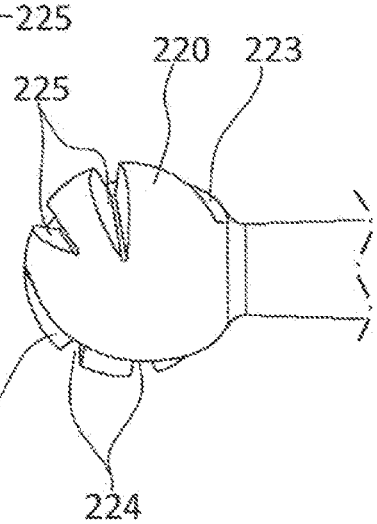
FIG. 4D

SURGICAL BUR

CROSS REFERENCE TO RELATED APPLICATIONS

This application is based on Japanese Patent Applications No. 2021-104515 filed on Jun. 24, 2021, the entire contents of which are incorporated herein by reference.

TECHNICAL FIELD

The present disclosure relates to a surgical bur which is a medical instrument for surgery.

BACKGROUND ART

In the related art, there is a medical instrument that excises tissue including a bone or a tumor by rotating a surgical bur including a cutting portion. JP-A-2013-138820 discloses a surgical bur used in this medical instrument including a shaft portion that rotates about a rotation axial line, and a cutting portion that is provided at a distal end of the shaft portion. The cutting portion has a spherical shape, and a cutting surface is formed by adhering diamond abrasive grains to a surface of the cutting portion. A surgeon uses the above-described surgical bur by attaching the surgical bur to a handpiece constituting the medical instrument, rotating the surgical bur, and pressing the rotating cutting surface against an object to be excised.

However, since the surgical bur described in JP-A-2013-138820 is used by rotating at a high speed from 20,000 rpm to 100,000 rpm, heat is generated due to friction between the cutting surface and the object to be excised. When the surgical bur heated by the friction approaches a periphery of a part to be cut, the heat may be conducted to the object. Therefore, careful operation is required. From such a background, there is a demand for a surgical bur having higher cooling efficiency in a field of performing surgery for removing tissue around an important portion including the nerves.

The present disclosure solves the above-described problems, and an object of the present disclosure is to provide a surgical bur having an improved cooling performance.

SUMMARY OF INVENTION

According to an aspect of the present disclosure, a surgical bur includes a shaft portion that rotates in a rotation direction about a rotation axial line of the surgical cutting bur, and a cutting portion that is provided at a distal end of the shaft portion. In the surgical bur, the cutting portion has a spherical shape, has abrasive grains on a surface of the cutting portion, and has a first vertical groove extending from a distal end side of the cutting portion in an axial direction.

According to the present disclosure, it is possible to improve the cooling performance of the surgical bur.

BRIEF DESCRIPTION OF DRAWINGS

FIGS. 4A, 4B, 4C, 4D, and 4E are views showing the cutting portion of the surgical bur according to the embodiment in which diamond abrasive grains of the cutting portion is omitted. FIG. 4A is a view showing the cutting portion as viewed from the axial direction, FIG. 4B is a view showing the cutting portion as viewed from a radial direction, FIG. 4C is a view showing the cutting portion viewed from a position rotated by 90 degrees around a distal end position M from a viewpoint of FIG. 4B, FIG. 4D is a view showing the cutting portion viewed from a position rotated by 90 degrees around the distal end position M from a viewpoint of FIG. 4C, and FIG. 4E is a view showing the cutting portion viewed from a position rotated by 90 degrees around the distal end position M from a viewpoint of FIG. 4D.

DESCRIPTION OF EMBODIMENTS

Hereinafter, an embodiment will be described with reference to the drawings. Here, as a medical instrument using a surgical bur according to the present disclosure, a surgical system which is a bone surgical instrument is exemplified. However, the medical instrument is not limited thereto, and may be a medical instrument for other purposes including dentistry.

<Surgical System>

Figure 1:
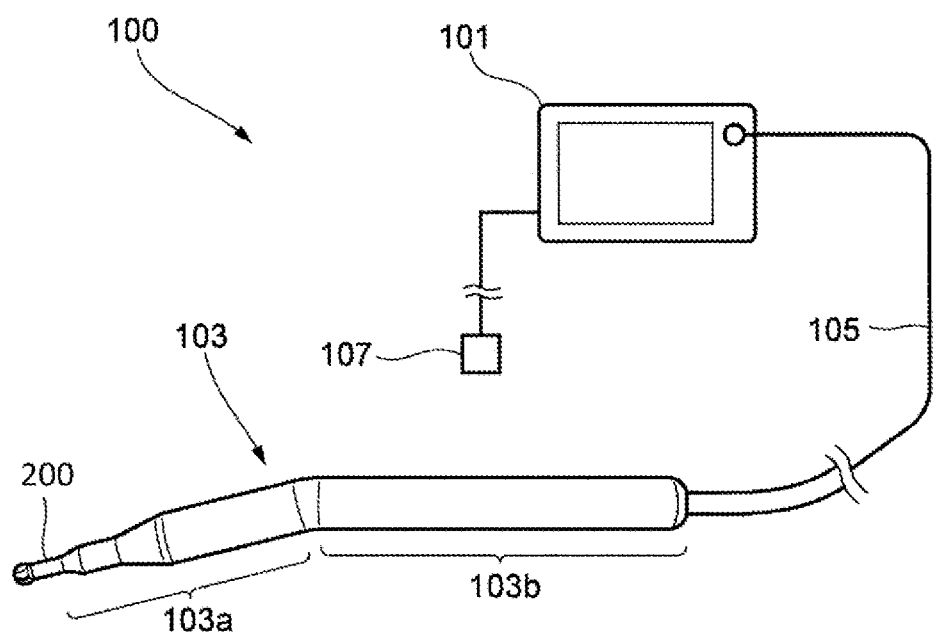
FIG. 1 is a schematic configuration diagram showing a surgical system according to an embodiment.

FIG. 1 is a schematic configuration diagram showing a surgical system 100. The surgical system 100 includes a control unit 101, a handpiece 103, a connection cable 105 that connects the handpiece 103 to the control unit 101, and a foot switch 107.

The handpiece 103 includes an attachment 103a and a grip portion 103b. A surgical bur 200 is detachably attached to the attachment 103a at a distal end of the handpiece 103. The handpiece 103 is provided with a power source including an air motor or an electric motor configured to rotationally drive the surgical bur 200. The power source is rotated or stopped by the foot switch 107 connected to the control unit 101. The control unit 101 is configured to control rotation of the handpiece 103. A hand switch configured to manually rotate or stop the drive source of the handpiece 103 may be provided on the handpiece 103, and the hand switch may be operated to rotate or stop the drive source. As long as an appropriate rotational driving force is applied to the surgical bur 200, the hand piece 103 may have a configuration other than the configuration used in the description of the present embodiment.

<Surgical Bur>

Figure 2:
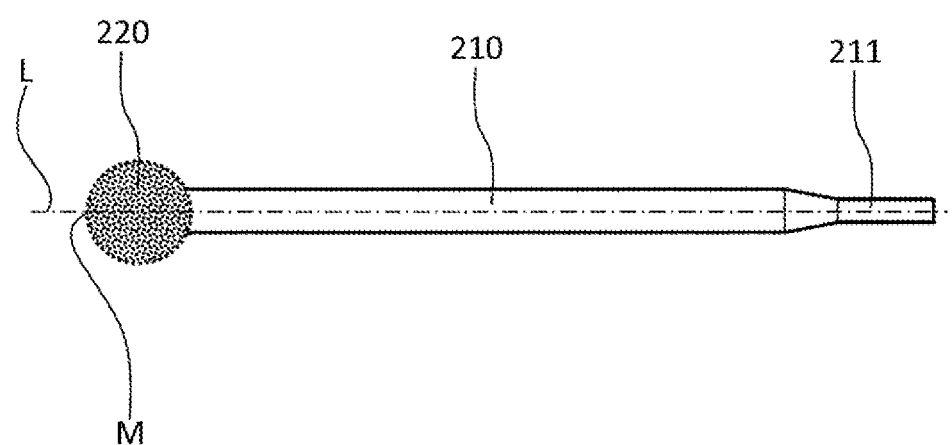
FIG. 2 is a configuration diagram showing a surgical bur according to the embodiment.

FIG. 2 is a configuration diagram showing the surgical bur 200. A virtual line indicating a rotation center of the surgical bur 200 is referred to as a rotation axial line L. The surgical bur 200 includes a shaft portion 210 having a rod shape along the rotation axial line L, and a cutting portion 220 that has a spherical shape and that is provided at one distal end of the shaft portion 210. The spherical shape means that, when the surgical bur 200 is rotated about the rotation axial line L, a shape of a curved surface included in the cutting portion 220 forms a sphere or a spheroid centered on the rotation axial line L.

The surgical bur 200 is formed of a hard material including stainless steel. Cemented carbide including tungsten carbide may be used. A connecting portion 211 that is connected and fixed to a rotating shaft of the handpiece 103 is provided at a base end of the shaft portion 210 which is opposite to the cutting portion 220. In the surgical bur 200 fixed to the rotating shaft, the cutting portion 220 and the shaft portion 210 rotate about the rotation axial line L by the handpiece 103.

In the surgical system 100, the surgical bur 200 is rotated by operating the foot switch 107 while holding the handpiece 103. Then, while the rotation of the cutting portion 220 is maintained, the operator pushes the cutting portion against an object to be excised including a bone or a tumor and appropriately moving the handpiece 103, and the object is cut. In the present embodiment, a rotation direction R of the surgical bur 200 is clockwise rotation as viewed from the operator holding the handpiece 103.

<Configuration of Cutting Portion>

Next, a configuration of the surgical bur 200 will be described with reference to FIGS. 2 to 4E. In the following description, in the surgical bur 200, along a direction (an axial direction) in which the rotation axial line L extends, a side on which the cutting portion 220 is located is referred to as a distal end side, and a side on which the connecting portion 211 is located is referred to as a rear end side. That is, in the cutting portion 220, along the rotation axial line L, a side on which the shaft portion 210 is located is the rear end side, and a side opposite to the shaft portion 210 is the distal end side. On a surface of a distal end of the cutting portion 220, a position is present through which the rotation axial line L passes. The position on the surface of the cutting portion 220 through which the rotation axial line L passes is referred to as a distal end position M. The same members or the same portions are denoted by the same reference numerals, and thus the description thereof will be omitted or simplified.

Figure 3:
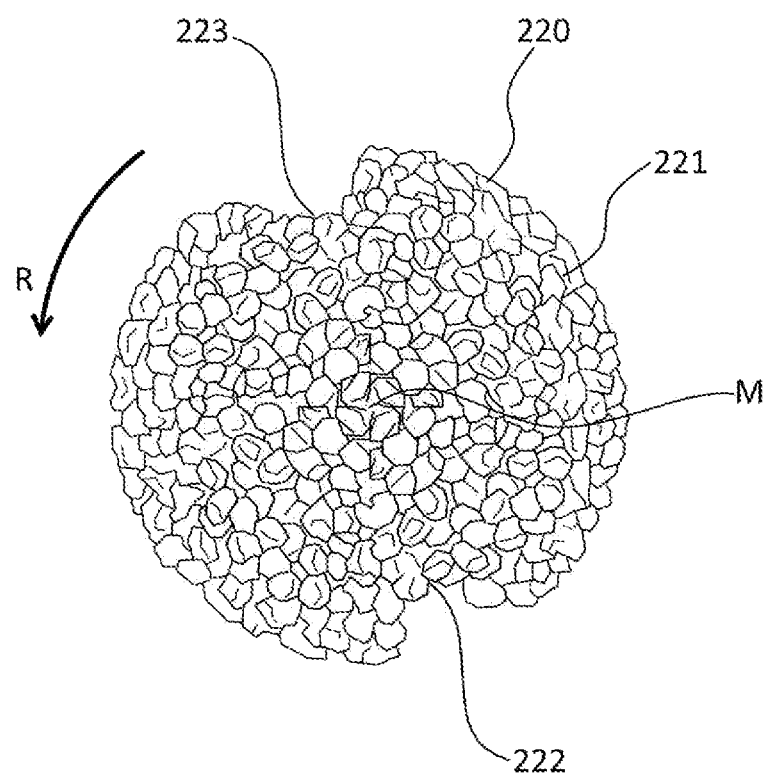
FIG. 3 is a view showing a cutting portion of the surgical bur according to the embodiment as viewed from an axial direction of a rotation axial line L.

FIG. 3 is a view showing the cutting portion 220 of the surgical bur 200 as viewed from the axial direction of the rotation axial line L. That is, FIG. 3 is a view showing the surgical bur 220 as viewed from a distal end. The cutting portion 220 is provided with diamond abrasive grains 221 by electrodeposition and the diamond abrasive grains 221 covers an entire spherical surface of the cutting portion 220. The diamond abrasive grains 221 are granules obtained by finely crushing diamond. On the surface of the cutting portion 220 to which the diamond abrasive grains 221 are electrodeposited, irregularities are formed by the diamond abrasive grains 221. The surgical bur 200 is configure to be rotated and brought into contact with a tissue including a bone or a tumor to be excised in order to scrape the tissue.

Next, the cutting portion 220 will be described with reference to FIGS. 3 to 4E. FIGS. 4A, 4B, 4C, 4D, and 4E are views in which the diamond abrasive grains 221 are omitted in order to explain a core shape of the cutting portion 220. FIG. 4A is a view showing the cutting portion 220 as viewed from the axial direction. FIG. 4B is a view showing the cutting portion 220 as viewed from a radial direction. FIG. 4C is a view showing the cutting portion 220 viewed from a position rotated by 90 degrees around the distal end position M from a viewpoint of FIG. 4B. FIG. 4D is a view showing the cutting portion 220 viewed from a position rotated by 90 degrees around the distal end position M from a viewpoint of FIG. 4C. FIG. 4E is a view showing the cutting portion 220 viewed from a position rotated by 90 degrees around the distal end position M from a viewpoint of FIG. 4D.

A first vertical groove 222 is formed in the cutting portion 220. The first vertical groove 222 is a part recessed from the surface of the cutting portion 220 and extending from the distal end toward the rear end. In other words, the first vertical groove 222 extends from the distal end to a side on which the shaft portion 210 is located in the cutting portion 220. A second vertical groove 223 is also formed in the cutting portion 220. The second vertical groove 223 is a part recessed from the surface of the cutting portion 220 and extending from the distal end toward the rear end side. In other words, the second vertical groove 223 extends from the side of the distal end to the side on which the shaft portion 210 is located in the cutting portion 220.

Here, the first vertical groove 222 and the second vertical groove 223 have substantially the same shape, and are provided at an equal interval in the rotation direction of the cutting portion 220. In other words, the first vertical groove 222 and the second vertical groove 223 are grooves having shapes that are point symmetric to each other with respect to the distal end position M in the cutting portion 220. The first vertical groove 222 and the second vertical groove 223 that extend in the axial direction are inclined in the rotation direction of the surgical bur 200 such that distal end side portions of the first vertical groove 222 and the second vertical groove 223 are located on a rotation direction side of a shaft side portions of the first vertical groove 222 and the second vertical groove 223 as shown in FIGS. 4A and 4D.

Next, first lateral grooves 224 extending from the first vertical groove 222 are formed in the cutting portion 220. The first lateral grooves 224 extend from the first vertical groove 222 in a direction opposite to the rotation direction of the surgical bur 200. Internal spaces of the first lateral groove 224 is connected to an internal space of the first vertical groove 222 are connected. In the present embodiment, two first lateral grooves 224 extending from the first vertical grooves 222 are formed with a given interval in a vertical direction.

Second lateral grooves 225 extending from the second vertical groove 223 are formed in the cutting portion 220. The second lateral grooves 225 extend from the second vertical groove 223 in the direction opposite to the rotation direction of the surgical bur 200. Internal spaces of the second lateral grooves 225 is connected to an internal space of the second vertical groove 223. In the present embodiment, two second lateral grooves 225 extending from the second vertical grooves 223 are formed with a given interval in the vertical direction.

Here, the first lateral grooves 224 and the second lateral grooves 225 do not overlap in the rotation direction. The first lateral grooves 224 and the second lateral grooves 225 are displaced in the vertical direction in order to avoid the overlapping in the rotation direction. A depth of each of the first lateral grooves 224 is smaller than a depth of the first vertical groove 222. In other words, the internal space of one of the first lateral grooves 224 is smaller than the internal space of the first vertical groove 222. Similarly, a depth of each of the second lateral grooves 225 is smaller than a depth of the second vertical groove 223. In other words, the internal space of one of the second lateral groove 225 is smaller than the internal space of the second vertical groove 224. The diamond abrasive grains are provided on the surface of the cutting portion 220 by electrodeposition. The diamond abrasive grains are also provided in each of the above-described grooves 222, 223, 224, 225 to an extent that the internal spaces of the grooves are not completely filled.

The surgical bur 200 implemented as described above is used in surgery as follows to excise a tissue including a bone or a tumor to be excised. First, an operator operates the foot switch 107 to drive an air motor or an electric motor to rotationally drive the surgical bur 200. Then, while cooling water is supplied to the cutting portion 220 of the rotating surgical bur 200, the cutting portion 220 is brought into contact with the object to be excised to excise the object.

While the cutting portion 220 is rotated, the diamond abrasive grains constituting the surface of the cutting portion 220 are brought into contact with the object to be excised, and the object is scraped. At this time, since the diamond abrasive grains are brought into contact with the object at a high speed, frictional heat is generated and a temperature of the cutting portion 220 rises. The operation is performed while the cooling water is supplied to the rotating cutting portion 220 in order to cool the cutting unit 220. Thereby, the cutting unit 220 does not become high temperature due to the frictional heat with the object.

Figure 5:
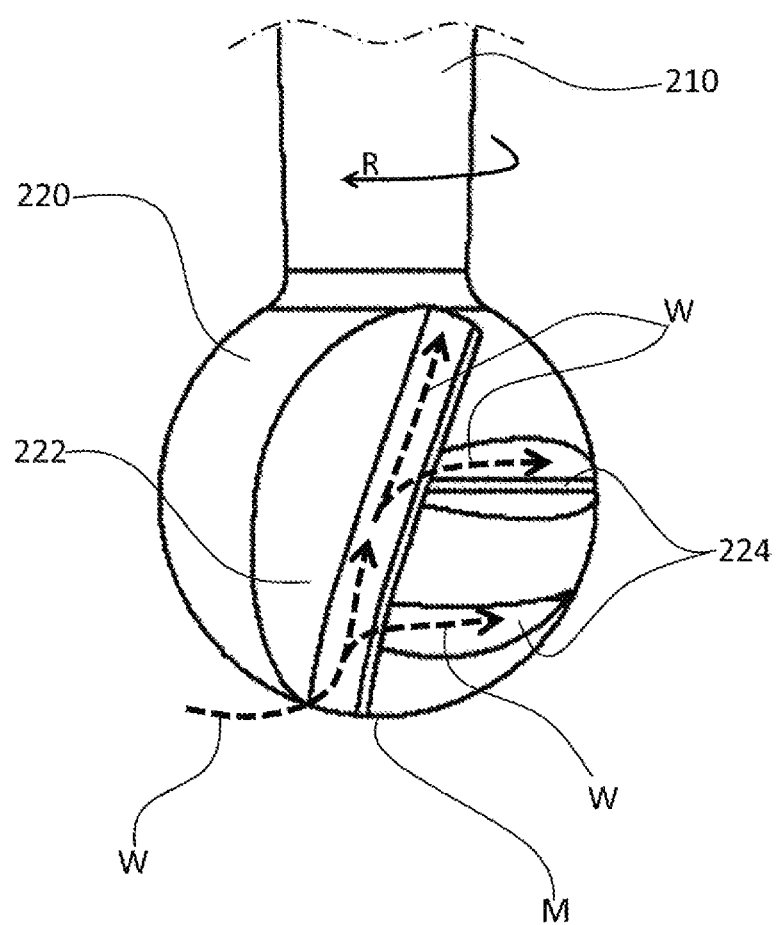
FIG. 5 is a view showing flow of cooling water for the cutting portion at the time of use of the surgical bur according to the embodiment.

Then, the supplied cooling water works on the cutting portion 220 during the excising operation as follows. FIG. 5 shows a flow W of the cooling water in the cutting portion 220 during the excising operation. The cutting portion 220 rotates in the supplied cooling water. The cooling water enters the inner spaces of the first vertical groove 222 and the second vertical groove 223, and the cooling is promoted in the axial direction of the cutting portion 220. The first vertical groove 222 and the second vertical groove 223 are regions recessed from the cutting portion 220. Since the cooling water is efficiently held inside the grooves and an area of contact between the cooling water and the cutting portion 220 becomes large, a cooling performance using the cooling water is improved.

The first vertical groove 222 and the second vertical groove 223 are inclined in the rotation direction of the surgical bur 200 such that the distal end portions of the first vertical groove 222 and the second vertical groove 223 is located on the rotation direction side of the shaft side portions of the first vertical groove 220 and the second vertical groove 223. That is, the first vertical groove 222 and the second vertical groove 223 form a spiral shape while extending from the distal end toward the shaft portion 210.

Accordingly, the rotation of the cutting portion 220 causes a force due to the rotation to act on the flow W of the cooling water that has entered the first vertical groove 222 and the second vertical groove 223. Accordingly, the flow W of the cooling water from the distal end toward the shaft portion 210 is generated along the inside of the grooves 222, 223. That is, in the cutting portion 220, the flow W of the cooling water in the axial direction that cools the cutting portion 220 is formed from the distal end toward the shaft portion 210, so that the cooling performance of the cutting portion 220 is improved.

Further, the first lateral grooves 224 extending from the first vertical groove 222 are formed in the cutting portion 220. The first lateral grooves 224 extend from the first vertical groove 222 in the direction opposite to the rotation direction of the surgical bur 200. The internal spaces of the first lateral grooves 224 is connected to the internal space of the first vertical groove 222. In this way, the first lateral grooves 224 and the first vertical groove 222 are connected, and the first lateral grooves 224 extend in the direction opposite to the rotation direction. Therefore, apart of the cooling water held inside the first vertical groove 222 forms the flow W in which the cooling water reaches the first lateral grooves 224 by the rotation of the cutting portion 220.

Accordingly, the flow W of the cooling water in the rotation direction from the first vertical groove 222 toward the first lateral grooves 224 is formed in the cutting portion 220, and the cooling performance is improved. The same effect as the first lateral grooves 224 and the first vertical groove 222 is obtained by the second lateral grooves 225 extending from the second vertical groove 223.

Here, each of the first lateral grooves 224 and the second lateral grooves 225 extends along the rotation direction from a corresponding one of the vertical grooves. The first lateral grooves 224 and the second lateral grooves 225 are formed in a positional relationship in which they are displaced in the axial direction so as not to overlap each other in the rotation direction of the cutting portion 220. In this way, since the lateral grooves 224, 225 are displaced in the axial direction in order to avoid the overlapping in the rotation direction, the cutting portion 220 is cooled in a wide range in the rotation direction.

In the present embodiment, the positional relationship between the first vertical groove 222 and the second vertical groove 223 and the positional relationship between the first lateral grooves 224 and the second lateral grooves 225 are each point symmetric with respect to the distal end position M. That is, the distal end position M is disposed between the first lateral grooves 224 and the second lateral grooves 225 as viewed from the axial direction. Since the cutting portion 220 is formed in this way, a weight of the cutting portion 220 is balanced with reference to the rotation axial line L. Accordingly, it is possible to reduce vibration of the cutting portion 220 when the surgical bur is rotated, and it is preferable for performing the excising operation.

What is claimed is:

1. A surgical bur comprising:
a shaft portion that rotates in a rotation direction about a rotation axial line; and
a cutting portion that is provided at a distal end of the shaft portion,
wherein the cutting portion has a spherical shape, has abrasive grains on a surface of the cutting portion, and has a first vertical groove extending from a distal end side of the cutting portion in an axial direction of the shaft portion.

2. The surgical bur according to claim 1,
wherein the cutting portion includes a first lateral groove connected to the first vertical groove.

3. The surgical bur according to claim 2,
wherein the first lateral groove extends from the first vertical groove in a direction opposite to the rotation direction.

4. The surgical bur according to claim 3,
wherein the cutting portion includes a second lateral groove which is displaced from the first lateral groove in the axial direction of the shaft portion.

5. The surgical bur according to claim 2,
wherein the cutting portion includes a second lateral groove which is displaced from the first lateral groove in the axial direction of the shaft portion.

6. The surgical bur according to claim 1,
wherein the cutting portion includes a second vertical groove which is displaced from the first vertical groove in the rotation direction.

7. The surgical bur according to claim 6,
wherein the first vertical groove is point symmetric to the second vertical groove with respect to a portion on the cutting portion intersecting the rotation axial line.

8. The surgical bur according to claim 1,
wherein the abrasive grains include diamond abrasive grains.

9. The surgical bur according to claim 1,
wherein the first vertical groove is inclined so that the first vertical groove includes:
a distal end portion which is farthest from the distal end of the shaft portion; and a base end portion which is closest to the distal end of the shaft portion, the base end portion being disposed at a rearward side of the distal end portion of the first vertical groove in the rotation direction.

\* \* \* \* \*